United States Patent [19]

Blum

[11] Patent Number: 5,871,518
[45] Date of Patent: Feb. 16, 1999

[54] SMOKING CESSATION LIGHTER AND METHOD

[76] Inventor: Alvin Seymour Blum, 2350 Del Mar Pl., Fort Lauderdale, Fla. 33301-1510

[21] Appl. No.: 10,531
[22] Filed: Jan. 22, 1998

Related U.S. Application Data

[60] Provisional application No. 60/036,390 Jan. 24, 1997.
[51] Int. Cl.⁶ ....................................... A61N 1/20
[52] U.S. Cl. ................................................. 607/58
[58] Field of Search ..................... 431/129, 130, 431/131, 144, 145, 157; 607/58

[56] References Cited

U.S. PATENT DOCUMENTS

| | | | |
|---|---|---|---|
| 3,885,576 | 5/1975 | Symmes | 131/170 A |
| 3,886,953 | 6/1975 | Pope | 131/170 A |
| 3,889,163 | 6/1975 | Symmes | 317/262 |
| 3,963,033 | 6/1976 | Pope | 131/170 A |
| 4,246,913 | 1/1981 | Ogden | 131/171 |
| 5,501,697 | 3/1996 | Fisher | 606/204 |

*Primary Examiner*—Scott Getzow
*Attorney, Agent, or Firm*—Alvin S. Blum

[57] ABSTRACT

A lighter for tobacco products suppresses the urge to smoke by operant conditioning. It delivers a shock to the user's hand when the lighter is extinguished. This generally happens when the first puffs of smoke are being inhaled. Inhalation of the smoke gives a positive reinforcement of the habit because of the pharmacologic effects of the smoke. The shock provides a negative or suppressive action at the same time. The anticipation of the shock will negate the anticipation of the relief the drugs in the smoke provide. In an alternative embodiment, the shock is applied at; the time of activation of the lighter. In yet another embodiment of the invention a negative stimulus is provided by a pin that pricks the user at the time of activation of the lighter.

20 Claims, 1 Drawing Sheet

SMOKING CESSATION LIGHTER AND METHOD

This application is based, upon Provisional Patent Application Ser. No. 60/036390 filed Jan. 24, 1997.

FIELD OF THE INVENTION

This invention relates to devices that break the tobacco smoking habit, and more particularly to a lighter for tobacco products that discourages the habit by administering an electric shock at a particular time.

BACKGROUND OF THE INVENTION

Smoking tobacco products is habit forming. Prolonged smoking leads to a very strong addiction. The reasons it is so addictive are many. A most important element of the addictive process is the positive reenforcement of smoking provided by the pharmacologic action of the inhaled smoke. An important component of the inhaled smoke is the vasoactive alkaloid nicotine. This is inhaled into the lungs and promptly diffuses across the alveolar walls and into the pulmonary capillaries. Since the diffusion distance is of the order of a micron, it is only a matter of seconds before the drug is delivered to the blood in the left ventricle and from there to the blood vessels and tissues of the entire body. The nicotine causes dilation of the blood vessels. In an addict deprived of smoking long enough for the drug effect to wear off, the blood vessels constrict, causing discomfort and anxiety. A few puffs administers enough drug to overcome the constriction, discomfort and anxiety. This is the positive reenforcement that teaches the smoker to crave the next cigarette. Other elements of the smoke or the smoking process may also contribute to the addictive process such as the feel of the smoke or other drugs we are not aware of. They may also promptly satisfy the craving of the smoker anxious for the next smoke.

Positive reenforcement strengthens an addiction. It is well known that habits and addictions can be overcome by a process of negative reenforcement or operant conditioning. For example, a patient who was seriously ill from uncontrollable hiccups that could not be stopped by any of the conventional methods was completely cured in one session by administering mild electrical shocks after every hiccup. The anticipation of the shock was apparently enough to overcome whatever mechanism was generating the hiccup.

Another patient with serious mental defficiency was biting her hands so badly that she was in danger of losing them. The habit was broken by administering a mild electrical shock every time she put her hand to her mouth.

This process of negative reinforcement or operant conditioning may be effective in breaking the smoking habit.

SUMMARY OF THE INVENTION

It is accordingly an object of the invention to provide a method and apparatus for breaking the smoking habit and addiction by application of negative reenforcement or operant conditioning methods including mild electrical shock. The smoking cessation process may be further enhanced by application of the shock at a particular time relative to the lighting and first puffs. Wherever the term cigarette is used, the word applies equally to the term cigar in this application. Although cigar smoke is not inhaled, the nicotine is absorbed through the oral mucosa. Where the term "he" is used it will apply equally to "she".

In a preferred embodiment, the electric shock apparatus is combined with a cigarette lighter. This ensures that the device will be in the smoker's hand whenever a cigarette is lit. The device applies a mild electric shock to the smoker's hand. The shook is preferably administered at the time the flame on the lighter is extinguished. Consider what is going on, consciously or unconsciously in the smoker's mind:

I sure do need a smoke.

Let me take out this cigarette.

Let me light it.

Let me take a few puffs and feel the relief from the anxiety.

Ah, that feels good. (Positive reinforcement). After it is lit, he pits out the lighter flame.

While using the smoking cessation lighter of the invention, something new has been added to what is going on in his mind:

I sure do need a smoke, but not a shook.

Let me take out a cigarette.

Let me light it.

Let me take a few puffs and feel the relief from the smoking need anxiety.

But the anxiety of shook anticipation mounts as he is faced with putting out the lighter and getting the shook. He finally puts out the lighter, feels the shook and the relief of the smoke is combined with the discomfort of the shook.

The next time he feels the smoke craving he also feels the fear of the shock that will accompany it. The negative reenforcement will overcome the positive reenforcement for many smokers, leading to breaking the smoking habit.

In lighters of the type where the thumb presses on a part during lighting and release of the thumb pressure turns off the lighter, a first conductive electrode is connected to the thumb actuator and a second electrode is connected to the part of the lighter held in the hand. A mild electric shock voltage is applied between these two electrode when thumb pressure is released. The shocking voltage will traverse only the hand, so that it will be unpleasant but not dangerous to the system. There is no need to connect electrodes to the smoker, grasping the lighter does that. A charging mechanism may be initiated by pressing the thumb and the shock application or discharge actuated by releasing the thumb. This greatly simplifies the mechanism and reduces battery drain.

In an alternative embodiment, the shock is applied when the lighter is on.

In an alternative embodiment, the aversive stimulus may be other unpleasant stimuli such as a pin prick.

These and other objects, advantages and features of the invention will become more apparent when the detailed description is considered in conjunction with the drawings, in which like elements are indicated by like reference characters in the various drawing figures.

DETAILED DESCRIPTION OF PREFERRED EMBODIMENTS

Figure 1:
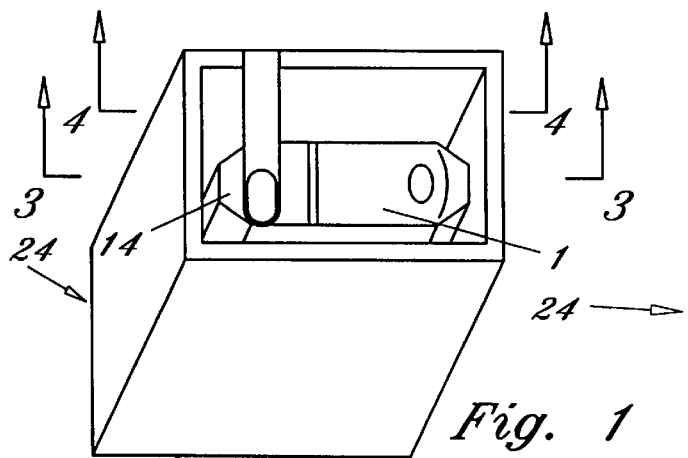
FIG. 1 is a perspective view of the apparatus of the invention.
Figure 2:
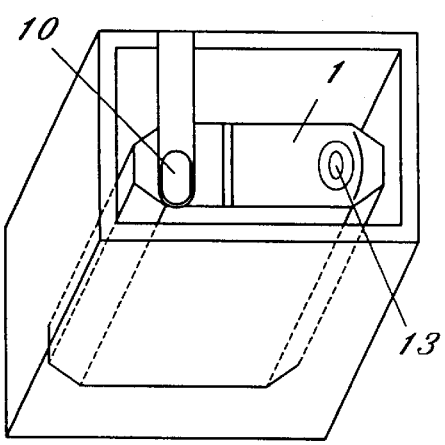
FIG. 2 is a perspective view as in FIG. 1 with portions shown in phantom.
Figure 3:
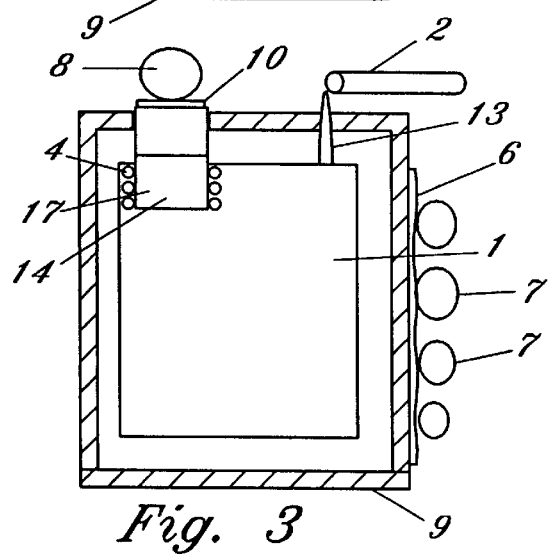
FIG. 3 is a sectional view taken through line 3—3 of FIG. 1.
Figure 4:
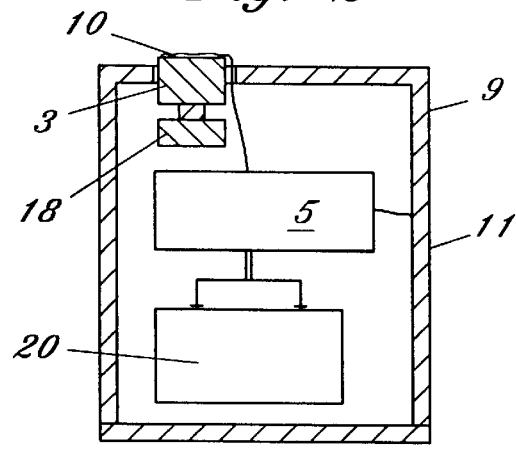
FIG. 4 is a sectional view taken through line 4—4 of FIG. 1.
Figure 5:
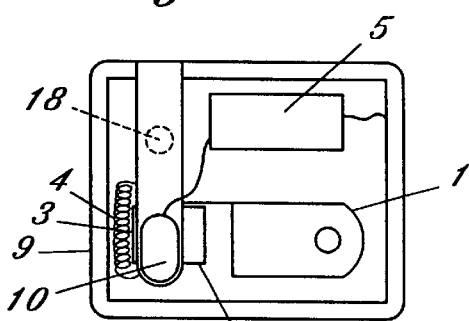
FIG. 5 is a top view of the apparatus of FIG. 1.

Referring now to FIGS. 1–5 and 7, the smoking cessation apparatus 24 comprises a combustion means 1 that may be any of the well known cigarette lighters such as the butane fueled lighters that employ a thumb operated gas pedal 14 that must be depressed to release gas and that is spring biased by spring 4 to close the valve and deactivate the flame 13 after the cigarette 2 is lit. The thumb pressure on gas pedal 14 may also operate a piezoelectric igniting source 17.

The electric shocking means 5 enclosed within housing 9 along with combustion means 1 is powered by battery 20. A large capacitor 19 is normally connected through single pole double throw (SPDT) switch 18 to the primary 25 of transformer 15. When the gas pedal 14 is depressed to activate the flame, the SPDT switch connects the battery to the capacitor, charging it up. When the pedal is released to extinguish the flame after lighting the cigarette, the switch returns by spring bias to the normal position shown, connecting the charged capacitor across the primary of the step up transformer 15.

A very high voltage appears momentarily across the secondary 26 of the transformer. This voltage is applied to a first conductive electrode 10 on the surface of the gas pedal to be in intimate contact with thumb on the pedal, and a second electrode 11 which may be on the surface of housing 9, or the housing may be made of a conductive material. A current path is thereby provided for the electric shock voltage between the thumb 8 and the fingers 7 or palm 6 of the hand holding the apparatus. This ensures that the shock will not go through the torso and the heart. By providing a fixed capacitance, the total shock energy that may be applied is limited to further ensure safety.

With this mechanism, the shock is not applied until the flame is extinguished, which may be most effective psychologically as well as ensuring that dropping the apparatus when shocked will not be a fire hazard. The SPDT switch may alternatively be a heat actuated switch so positioned as to be heated by the flame.

Figure 8:
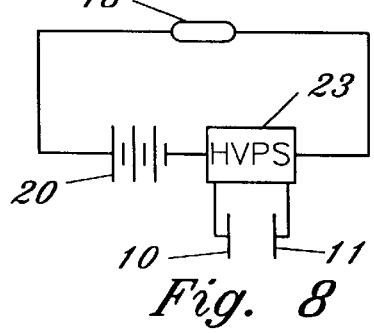
FIG. 8 is a schematic diagram of another embodiment of the shocking means.

FIG. 8 shows an alternative shocking means in which the shock is applied when the flame is burning. The switch 18 connects the battery 20 to the high voltage power supply (HVPS) 23 when the gas pedal is depressed and the flame is on. The HVPS applies shocking voltage to the electrodes 10,11 while the flame is lit and stops when the flame is out. The switch 18 may be a pressure actuated. SPST switch normally open, or it may be a heat actuated switch or thermister heated by the flame.

Figure 6:
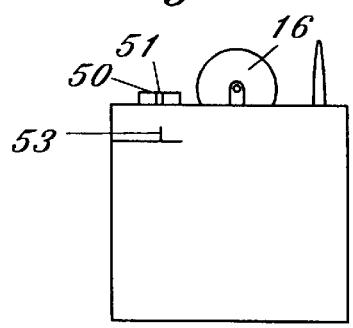
FIG. 6 is a side view of another embodiment of the invention.
Figure 7:
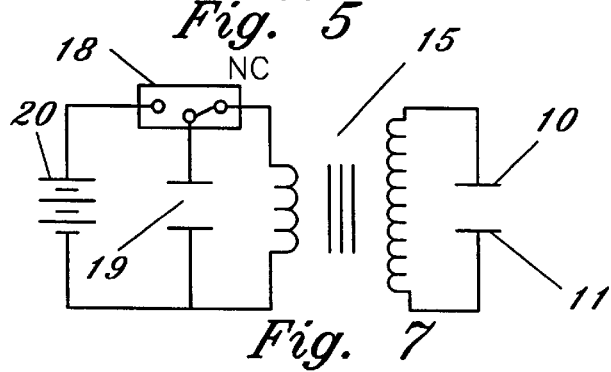
FIG. 7 is a schematic diagram of the shocking means of FIG. 1.

FIG. 6 shows a gas fuel lighter with a flint and steel ignition mechanism 16 that may also be employed. Either type of lighter or others well known and commercially available may be received in the housing 9 so that manufacture of the apparatus is greatly simplified.

The negative reenforcement or aversive stimulus may take forms other than electric shock. In the embodiment shown in FIG. 6, the gas pedal 50 is provided with a small aperture 51 that receives a sharp fixed pin 53 whenever the pedal 50 is depressed by the user's thumb during lighter activation to create the gas flame. The pin passes through the pedal and delivers a painful and unpleasant stimulus by pricking the thumb. Anticipation of this aversive stimulus will suppress the urge to light up a smoke.

The above disclosed invention has a number of particular features which should preferably be employed in combination although each is useful separately without departure from the scope of the invention. While I have shown and described the preferred embodiments of my invention, it will be understood that the invention may be embodied otherwise than as herein specifically illustrated or described, and that certain changes in the form and. arrangement of parts and the specific manner of practicing the invention may be made within the underlying idea or principles of the invention.

What is claimed is:

1. A method for supressing, in a smoker, the desire to smoke tobacco products comprising the steps of:
    a) providing a combustion means for lighting a tobacco product, including means for activating and deactivating the combustion means;
    b) providing an electric shock means for applying a shock to the smoker; and
    c) applying an electric shock from the shock means to the smoker upon activating or deactivating the combustion means.

2. The method of claim 1, in which the combustion means is held by a hand of the smoker and the shock is applied to the hand.

3. The method of claim 2, in which the electric shock means is operatively connected to the activating or deactivating means for automatically actuating the electric shock means.

4. An apparatus for supressing, in a smoker, the desire to smoke tobacco products, the apparatus comprising:
    a) a combustion means for lighting a tobacco product;
    b) activating means operatively connected to the combustion means for activating the combustion means;
    c) deactivating means operatively connected to the combustion means for deactivating the combustion means;
    d) shocking means for applying an electric shock to the smoker, operatively connected to the combustion means adapted for automatically applying the shock in timed relationship to the operation of the combustion means.

5. The apparatus according to claim 4, in which the combustion means and the shocking means are combined in a hand held unit and the shocking means is constructed for applying the electric shock across portions of the hand that holds the unit.

6. The apparatus according to claim 5, in which a housing incorporates the shocking means and receives a ready made lighter, the lighter being the combustion means, the housing provided with electrodes for contacting portions of the hand and a switching assembly that operates the shocking means and the lighter simultaneously.

7. The apparatus according to claim 6, in which the deactivating means and the shocking means are operatively connected for applying the shock and deactivating the combustion means substantially simultaneously.

8. The apparatus according to claim 6, in which the activating means and the shocking means are operatively connected for applying the shock and activating the combustion means substantially simultaneously.

9. The apparatus according to claim 5, in which the heat generated by the combustion means actuates the shocking means.

10. A method for supressing, in a smoker, the desire to smoke tobacco products comprising the steps of:
    a) providing a combustion means for lighting a tobacco product, including means for activating and deactivating the combustion means;

b) providing stimulus means for applying an unpleasant stimulus to the smoker; and c) applying the unpleasant stimulus from the stimulus means to the smoker upon activation or deactivation of the combustion means.

11. The method of claim 10, in which the combustion means is to be held in a hand of the smoker, and the stimulus is applied to the hand.

12. The method of claim 11, in which the stimulus is a pin prick that is administered upon activation of the combustion means.

13. The method of claim 11, in which the stimulus is an electric shock.

14. An apparatus for supressing, in a smoker, the desire to smoke tobacco products, the apparatus comprising:

a) a combustion means for lighting a tobacco product;

b) activating means operatively connected to the combustion means for activating the combustion means;

c) deactivating means operatively connected to the combustion means for deactivating the combustion means; and d) stimulus means for applying an unpleasant stimulus to the smoker, the stimulus means being operatively connected to the combustion means and adapted for applying the stimulus in timed relationship to the operation of the combustion means.

15. The apparatus according to claim 14, in which the stimulus and the combustion means are combined in a unit constructed so as to be held in a hand and so as to apply the stimulus to the hand upon activation of the combustion means.

16. The apparatus according to claim 15, in which the stimulus is an electric shock.

17. The apparatus according to claim 15, in which the stimulus is a pin prick.

18. The apparatus according to claim 14, in which the stimulus means and the combustion means are combined in a unit constructed so as to be held in a hand and so as to apply the stimulus to the hand upon deactivation of the combustion means.

19. The apparatus according to claim 18, in which the stimulus is an electric shock.

20. The apparatus according to claim 18, in which the stimulus is a pin prick.

* * * * *